United States Patent [19]

Portnoy

[11] 4,113,724

[45] Sep. 12, 1978

[54] ARYLTHIODICYANOPYRAZINES AS PLANT DISEASE CONTROL AGENTS

[75] Inventor: Robert Charles Portnoy, Wilmington, Del.

[73] Assignee: E. I. Du Pont de Nemours and Company, Wilmington, Del.

[21] Appl. No.: 805,150

[22] Filed: Jun. 9, 1977

[51] Int. Cl.² .................................... C07D 241/24
[52] U.S. Cl. ................................ 544/408; 424/250
[58] Field of Search .................. 260/250 BN; 424/250

[56] References Cited

U.S. PATENT DOCUMENTS 3,940,392 2/1976 Johnston ....................... 260/250 BN Primary Examiner—Donald G. Daus
Assistant Examiner—Lisa Jones

[57] ABSTRACT

Compounds of the Formula (I)

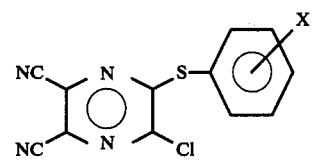

where X is hydrogen, methoxy or alkyl of 1–4 carbon atoms
are effective in controlling plant fungus diseases.

6 Claims, No Drawings

4,113,724

ARYLTHIODICYANOPYRAZINES AS PLANT DISEASE CONTROL AGENTS

BACKGROUND OF THE INVENTION

This invention relates to plant disease control agents and, more particularly, to compounds of formula (I)

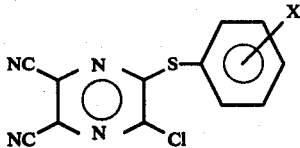

wherein X is hydrogen, methoxy or alkyl of 1–4 carbon atoms which are useful in controlling a broad spectrum of plant fungus diseases.

U.S. Pat. No. 3,879,394 discloses and claims the synthesis of aminodicyanopyrazines. The use of these compounds for plant disease control is disclosed in U.S. Pat. No. 4,054,655. There are no known references which teach or suggest that compounds of this invention would be effective against plant fungus diseases.

SUMMARY OF THE INVENTION

Compounds of the formula (I)

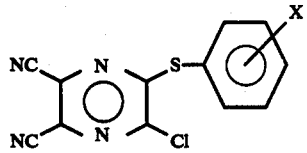

where X is hydrogen, methoxy or alkyl of 1–4 carbon atoms are useful as fungicides in treating such plant diseases as apple scab, tomato late blight and sugarbeet Cercospora. Particularly preferred for their fungicidal activity are 5-chloro-6-(phenylthio)-2,3-pyrazinedicarbonitrile 5-chloro-6-[(4-methylphenyl)thio]-2,3-pyrazinedicarbonitrile 5-chloro-6-[(2-methylphenyl)thio]-2,3-pyrazinedicarbonitrile 5-chloro-6-[(3-methylphenyl)thio]-2,3-pyrazinedicarbonitrile 5-chloro-6-[(3-methoxyphenyl)thio]-2,3-pyrazinedicarbonitrile There is further provided in the present invention a fungicidal composition in which the compound of formula (I) is the active ingredient.

Also provided in the present invention is a process for making arylthiodicyanopyrazines of formula (I).

DETAILED DESCRIPTION OF THE INVENTION

According to this invention, it has been discovered that arylthiodicyanopyrazines of the formula (I)

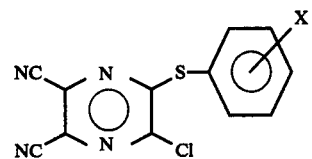

where X is hydrogen, methoxy or alkyl of 1–4 carbon atoms are effective in controlling a broad spectrum of plant fungus diseases, such as apple scab caused by *Venturia inaequalis*, potato and tomato late blight caused by *Phytophthora infestans*, sugarbeet Cercospora leaf spot caused by *Cercospora beticola* and gray mold of vegetables, fruits and ornamentals caused by *Botrytis cinerea*. This is only a representative sample of the plant diseases that can be controlled by the compounds of this invention. These compounds are also effective against other related plant diseases.

Disease control is accomplished by applying a fungicidally effective amount of compound to the portion of the plant to be protected. Preferred rates of application for these compounds to foliage, stems, and/or fruit of living plants range from 0.05 to 20 kilograms of active ingredient per hectare. More preferred rates are in the range of 0.1 to 10 kilograms per hectare. The most preferred rates are in the range of 0.2 to 5 kilograms per hectare. The optimum amount within this range depends upon a number of variables which include, but are not limited to, the disease to be controlled, weather conditions expected, type of crop, stage of development of the crop, and interval between applications. Applications may need to be repeated one or more times at intervals of 1 to 60 days.

Preferred rates for application to seeds, tubers, bulbs, or other plant reproductive parts range from 0.5 to 100 grams of the compound per kilogram of plating material treated. More preferred rates are in the range of 1 to 75 grams of active compound per kilogram. The most preferred rates are in the range of 2 to 50 grams per kilogram.

Compositions of this invention may contain, in addition to the arylthiodicyanopyrazines other insecticides, miticides, bactericides, nematicides, fungicides, or other agricultural chemicals such as fruit set agents, fruit thinning compounds, fertilizer ingredients, and the like. The additional agricultural chemicals are employed in mixtures or combinations in amounts ranging from one-tenth to twenty times that of the compounds of this invention. Following are typical agricultural chemicals that may be included in compositions or added to sprays containing one or more of the active compounds of this invention:

bis(dimethylthiocarbamoyl)disulfide; or tetramethylthiuram disulfide (thiram);

metal salts of ethylenebisdithiocarbamic acid or propylenebisdithiocarbamic acid, e.g. manganese, zinc, iron and sodium salts (maneb or zineb);

n-dodecylguanidine acetate (dodine);

N-(trichloromethylthio)phthalimide (folpet);

N-[(trichloromethyl)thio]-4-cyclohexene-1,2-dicarboximide (captan);

cis-N-[(1,1,2,2-tetrachloroethyl)thio]-4-cyclohexene-1,2-dicarboximide (captafol);

2,4-dichloro-6-(o-chloroanilino)-α-triazine ("Dyrene");

3,3'-ethylenebis(tetrahydro-4,6-dimethyl-2H-1,3,5-thiadiazine-2-thione), (milneb);
triphenyltin hydroxide (fentin hydroxide);
triphenyltin acetate (fentin acetate);
N'-dichlorofluoromethylthio-N,N-dimethyl-N'-phenylsulfamide (dichlofluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate;
1,2-bis(3-methoxycarbonyl-2-thioureido)benzene (methyl thiophanate);
2-cyano-N-(ethylcarbamoyl)-2-methoxyiminoacetamide.

The agricultural chemicals listed above are merely exemplary of compounds that may be mixed with the active compounds of this invention to broaden the spectrum of disease control.

This invention is further illustrated by the following examples.

EXAMPLE 1

Compounds of this invention were dissolved in acetone in an amount equal to 10% of the final volume and then suspended at a concentration of 80 ppm in purified water containing 250 ppm of the surfactant Trem ® 014 which consists of polyhydric alcohol esters. This suspension was sprayed to the point of run-off on seedling apple plants growing in pots and trained to a single shoot. The following day the apple seedlings were inoculated with a spore suspension of the fungus *Venturia inaequalis* and incubated in a saturated humidity chamber at 20° C for 24 hours, and then in a greenhouse for an additional 11 days. Disease ratings were made of two susceptible leaves on each of four replicate plants for each treatment, and percent control was calculated by the following formula:

$$100 - \left[ \frac{\text{disease rating on treated}}{\text{disease rating on untreated}} \times 100 \right] = \% \text{ control}$$

The results of this test are shown in Table 1.

TABLE 1

| Compound | Percent Apple Scab Control |
| --- | --- |
| 5-Chloro-6-(phenylthio)-2,3-pyrazinedicarbonitrile | 100 |
| 5-Chloro-6-[(4-methylphenyl)thio]-2,3-pyrazinedicarbonitrile | 100 |
| 5-Chloro-6-[(2-methylphenyl)thio]-2,3-pyrazinedicarbonitrile | 99 |
| 5-Chloro-6-[(3-methylphenyl)thio]-2,3-pyrazinedicarbonitrile | 100 |
| 5-chloro-6-[(3-methoxyphenyl)thio]-2,3-pyrazinedicarbonitrile | 95 |
| 5-Chloro-6-[(4-methoxyphenyl)thio]-2,3-pyrazinedicarbonitrile | 98 |

EXAMPLE 2

Compounds of this invention were dissolved in acetone and then suspended at a concentration of 80 ppm in purified water containing 250 ppm of the surfactant Trem ® 014. This suspension was sprayed to the point of run-off on tomato plants growing in pots in a greenhouse. Six hours later the plants were inoculated with a spore suspension of the fungus *Phytophthora infestans* and incubated in a saturated humidity at 20° C for 20 hours and then in a greenhouse an additional 4 days. Disease ratings were made for each treatment, and percent control was calculated by the following formula:

$$100 - \left[ \frac{\text{disease rating on treated}}{\text{disease rating on untreated}} \times 100 \right] = \% \text{ control}$$

The results of this test are shown in Table 2.

TABLE 2

| Compound | Percent Tomato Late Blight Control |
| --- | --- |
| 5-Chloro-6-(phenylthio)-2,3-pyrazinedicarbonitrile | 91 |
| 5-Chloro-6-[(4-methylphenyl)thio]-2,3-pyrazinedicarbonitrile | 93 |
| 5-Chloro-6-[(2-methylphenyl)thio]-2,3-pyrazinedicarbonitrile | 89 |
| 5-Chloro-6-[(3-methoxyphenyl)thio]-2,3-pyrazinedicarbonitrile | 91 |

EXAMPLE 3

Four-week-old sugarbeets were sprayed uniformly to the point of run-off with a dispersion consisting of acetone, purified water, 500 ppm of the surfactant Trem ® 014 and the compounds of this invention at a concentration of 100 ppm. After 24 hours, the sugarbeets were inoculated with a spore suspension of *Cercospora beticola* and incubated in a transparent, saturated humidity chamber at 22° to 26° C for 72 hours. After 21 days of further incubation in the greenhouse, disease ratings were made by counting the number of lesions on the two most severely infected leaves on each of three replicate plants for each treatment, and percent control was calculated by the following formula:

$$100 - \left[ \frac{\text{No. lesions on treated}}{\text{No. lesions on untreated}} \times 100 \right] = \% \text{ control}$$

The results of this test are shown in Table 3.

TABLE 3

| Compound | Percent *Cercospora* Leaf Spot Control |
| --- | --- |
| 5-Chloro-6-(phenylthio)-2,3-pyrazinedicarbonitrile | 99 |
| 5-Chloro-6-[(4-methylphenyl)thio]-2,3-pyrazinedicarbonitrile | 94 |
| 5-Chloro-6-[(2-methylphenyl)thio]-2,3-pyrazinedicarbonitrile | 82 |
| 5-Chloro-6-[3-methylphenyl)thio]-2,3-pyrazinedicarbonitrile | 98 |

EXAMPLE 4

Two-week-old broadbean plants were sprayed uniformly to the point of run-off with a dispersion consisting of acetone, purified water, 500 ppm of the surfactant Trem ® 014 and the compounds of this invention at a concentration of 500 ppm. After 24 hours, the plants were inoculated with a spore suspension of the fungus *Botrytis cinerea* and incubated in a transparent, saturated humidity chamber at 22° to 26° C for 72 hours. After 2 days of further incubation in a greenhouse, disease ratings were made by a visual estimate of the percentage of diseased tissue on each of 3 replicate plants for each treatment and percent control was calculated by the following formula:

$$100 - \left[ \frac{\text{disease rating on treated}}{\text{disease rating on untreated}} \times 100 \right] = \% \text{ control}$$

The results of this test are shown below.

| Compound | Percent *Botrytis Cinerea* Control |
|---|---|
| 5-Chloro-6(phenylthio)-2,3-pyrazine-dicarbonitrile | 92 |
| 5-Chloro-6-[(4-methylphenyl)thio]-2,3-pyrazinedicarbonitrile | 88 |

Useful formulations of the compounds of this invention can be prepared in conventional ways. These include dusts, granules, pellets, solutions, suspensions, emulsions, wettable powders, emulsifiable concentrates and the like. Many of these may be applied directly. Sprayable formulations can be used at volumes of from a few to several hundred liters per hectare. High strength compositions are primarily used as intermediates for further formulation. The formulations may contain about 1 to 99% by weight of active ingredient(s) and at least one of (a) about 0.1 to 20% surfactant(s) and (b) about 1 to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20-90 | 0-79 | 1-10 |
| Oil Suspensions, Emulsions, Solutions (including Emulsifiable Concentates) | 5-50 | 40-95 | 0-50 |
| Aqueous Suspension Concentrates | 10-50 | 40-89 | 1-20 |
| Dusts | 1-25 | 70-99 | 0-5 |
| Granules and Pellets | 1-95 | 5-99 | 0-50 |
| High Strength Compositions | 90-99 | 0-10 | 0-2 |

The levels of active ingredient can be adjusted higher or lower than the preferred ranges depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers", MC Publishing Company, Ridgewood, New Jersey, as well as Sisely and Wood, "Encyclopedia of Surface Active Agents", Chemical Publ. Co. Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer-, pin-, or fluid energy mill. Suspensions are prepared by wet milling (see, for example, Littler, U.S. Pat. No. 3,060,084). Granules and pellets can be made by spraying the active material upon preformed granular carriers or by agglomeration techniques.

In formulations containing water, such as emulsions and water suspensions, it is preferred to maintain the pH of the formulation between about 5 and 7 to improve stability of the active chemical during storage. Both alkaline and acidic hydrolysis of the compounds of this invention are more rapid under pH conditions outside this range. A convenient method for adjusting the pH of the formulations within this range is the use of small quantities of dilute aqueous caustic or phosphoric acid solutions and buffers.

This invention is further illustrated by the following examples.

EXAMPLE 5

Wettable Powder

| | |
|---|---|
| 5-Chloro-6-(phenylthio)-2,3-pyrazine-dicarbonitrile | 40% |
| Dioctyl sodium sulfosuccinate | 1.5% |
| Sodium ligninsulfonate | 3% |
| Low Viscosity methyl cellulose | 1.5% |
| Attapulgite | 54% |

The ingredients are thoroughly blended, passed through a fluid mill to produce an average particle size under 15 microns in diameter, reblended, and sifted through a U.S.S. No. 50 sieve (0.3 mm opening) before packaging.

All compounds of this invention may be formulated in the same manner.

EXAMPLE 6

Wettable Powder

| | |
|---|---|
| 5-Chloro-6-[(4-methylphenyl)thio]-2,3-pyrazinedicarbonitrile | 80% |
| Sodium Alkylnaphthalenesulfonate | 2% |
| Sodium Ligninsulfonate | 2% |
| Synthetic Fine Silica | 3% |
| Kaolinite | 13% |

The ingredients are blended, hammer milled and then passed through a fluid mill to produce particles below 10 microns in diameter. After final blending, the product is packaged.

EXAMPLE 7

Dust

| | |
|---|---|
| 5-Chloro-6-[(2-methylphenyl)thio]-2,3-pyrazinedicarbonitrile | 10% |
| Attapulgite | 10% |
| Pyrophyllite | 80% |

The active ingredient is blended with attapulgite and passed through a hammer mill to produce particles mostly all of which are below 50 microns in diameter. The ground concentrate is then blended with powdered pyrophyllite and packaged.

EXAMPLE 8

Emulsifiable Concentrate

| | |
|---|---|
| 5 Chloro-6-[(3-methoxyphenyl)thio]-2,3-pyrazinedicarbonitrile (active ingredient) | 25% |
| blend of oil soluble sulfonates with polyoxyethylene ethers | 5% |
| xylene | 70% |

The ingredients are combined and stirred with gentle warming to speed solution. A fine screen filter is included in packaging operation to insure the absence of any extraneous undissolved material in the product.

EXAMPLE 9

Aqueous Suspension

| | |
|---|---|
| 5-Chloro-6-[(4-methylphenyl)thio]-2,3-pyrazinedicarbonitrile | 20.0% |
| Bentonite-type Clay | 3.0% |
| Crude calcium ligninsulfonate | 3.0% |
| Dioctylsodiumsulfosuccinate | 0.5% |
| Glycerine | 25.0% |
| Water | 48.5% |

The ingredients are ground together in a ball or roller mill until the solid particles have been reduced to diameters under 10 microns.

EXAMPLE 10

Oil Suspension

| | |
|---|---|
| 5-Chloro-6-[(3-methylphenyl)thio]-2,3-pyrazinedicarbonitrile | 25% |
| Polyoxyethylene sorbitol hexaoleate | 5% |
| Hydrocarbon spray oil (70 S.U.S.) | 70% |

The ingredients are ground together in a sand mill until the particles are under about 5 microns in diameter. The resulting thick suspension may be applied directly, but preferably after extension with oil or water.

Synthesis

Starting material for preparing the arylthiodicyanopyrazines of this invention is 5,6-dichloro-2,3-pyrazinedicarbonitrile, obtained by reacting 1,4,5,6-tetrahydro-5,6-dioxo-2,3-pyrazine-dicarbonitrile with thionyl chloride. This process is disclosed in U.S. Pat. No. 3,879,394 issued Apr. 22, 1975.

The arylthiopyrazines of this invention cannot be prepared satisfactorily by methods known in the art. They are prepared from 5,6-dichloro-2,3-pyrazinedicarbonitrile by an improved two-step process shown by diagram in Formula 1.

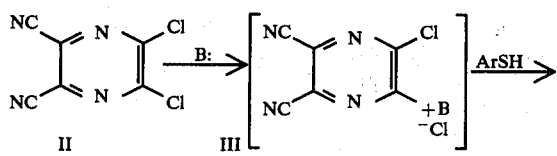

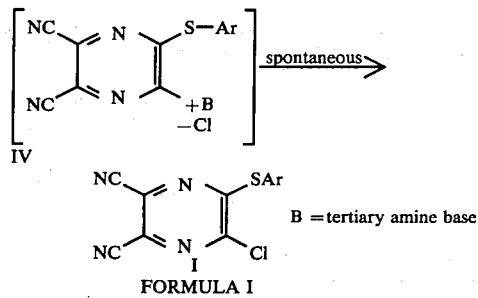

FORMULA I

B = tertiary amine base

The steps which characterize this process may be carried out in succession in a single reaction vessel without isolating the intermediate materials. To the starting material II mixed with a suitable solvent is added a tertiary amine base III. After sufficient time for complete reaction between the pyrazine and base, i.e., about 1 minute to 60 minutes, exactly one equivalent of a thiophenol IV chosen to correspond to one of the described products, is added in one portion. After completion of the reaction, the desired product I is isolated and purified by recrystallization or chromatography.

The solvent used in this process must be polar, aprotic, and capable of dissolving the salt formed by reaction of the pyrazine and the amine base. For this purpose the halogenated hydrocarbon solvents such as 1,2-dichloroethane or chloroform are especially suitable. Pyridine is the preferred tertiary amine base for reasons of economy and convenience. Substituted pyridines may also be used. The base may be used in either stoichiometric equivalent or excess quantity. The reaction between the dichlorodicyanopyrazine and the amine base may be carried out at any convenient temperature from −35° C to the boiling point of the solvent. Ambient temperature is most preferable because of reaction rate and economy. The temperature during the addition of the thiophenol may be held at any point between −35° and 0° C. The lower temperatures are preferred to give the best yield of the desired products. The process of this invention is further illustrated by the following examples.

EXAMPLE 11

5-Chloro-6-[4-(methylphenyl)thio]-2,3-pyrazinedicarbonitrile

Pyridine (0.79 g) was mixed with a solution of 2.00 g of 2,3-dichloro-5,6-dicyanopyrazine in 80 ml of 1,2-dichloroethane. After 15 minutes this mixture, protected from moisture, was cooled to −30° C, and 1.24 g of p-thiocresol was added in one portion. The temperature was maintained at −30° for 0.5 hour and then was allowed to return to ambient over the course of 2 hours. The mixture was then washed with water to remove pyridine hydrochloride, dried over MgSO₄, and concentrated on a rotary evaporator to a solid residue. This was recrystallized from alcohol to give 1.4 g of bright yellow crystals mp 125°–128°, which were shown by NMR, mass spectrophotometry and gas chromatography to be a pure sample of the desired material.

EXAMPLE 12

5-Chloro-6-[(3-methylphenyl)thio]-2,3-pyrazinedicarbonitrile

Pyridine (2.37 g) was mixed rapidly with a solution of 6.00 g of 2,3-dichloro-5,6-dicyanopyrazine in 240 ml of 1,2-dichloroethane. After 15 minutes the well stirred mixture, protected from moisture, was cooled to −30° and 3.72 g of m-thiocresol was added in one portion. The temperature was maintained at −30° for 0.5 hour and then was allowed to return to ambient over the course of 2 hours. The mixture was then washed with water to remove pyridine hydrochloride, dried over MgSO$_4$, and concentrated on a rotary evaporator to a solid residue. The residue was purified by the technique of dry column chromatography using silica gel adsorbent and 1-chlorobutane as solvent and eluent. The yield of pure product was 6.9 g, mp 117°–119°.

Some further examples of this process for preparing compounds of this invention are given in Table 4.

TABLE 4

| Example | X | mp° | Purification Method |
|---|---|---|---|
| 13 | H | 131–133 | Recrystallization (Alcohol) |
| 14 | 3-OCH$_3$ | 101–104 | Recrystallization |

TABLE 4-continued

| Example | X | mp° | Purification Method |
|---|---|---|---|
|  |  |  | (Alcohol) |
| 15 | 2-CH$_3$ | 124–126 | Column Chromatography |
| 16 | 4-C(CH$_3$)$_3$ | 138–140 | Recrystallization (CH$_3$CN/H$_2$O) |

What is claimed is:

1. A compound of the formula

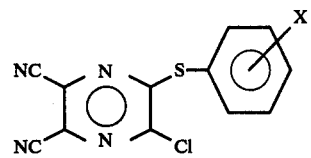

where X is hydrogen, methoxy or alkyl of 1–4 carbon atoms.

2. The compound of claim 1 which is 5-chloro-6-(phenylthio)-2,3-pyrazinedicarbonitrile.

3. The compound of claim 1 which is 5-chloro-6-[(4-methylphenyl)thio]-2,3-pyrazinedicarbonitrile.

4. The compound of claim 1 which is 5-chloro-6-[(2-methylphenyl)thio]-2,3-pyrazinedicarbonitrile.

5. The compound of claim 1 which is 5-chloro-6-[(3-methylphenyl)thio]-2,3-pyrazinedicarbonitrile.

6. The compound of claim 1 which is 5-chloro-6-[(3-methoxyphenyl)thio]-2,3-pyrazinedicarbonitrile.

* * * * *